United States Patent
Buelna et al.

(10) Patent No.: US 11,382,515 B2
(45) Date of Patent: Jul. 12, 2022

(54) RENAL DENERVATION USING NERVE FLUORESCING DYE

(71) Applicant: Verve Medical, Inc., Scottsdale, AZ (US)

(72) Inventors: Terrence J. Buelna, Santa Barbara, CA (US); Adam Gold, Scottsdale, AZ (US)

(73) Assignee: Verve Medical, Inc., Scottsdale, AZ (US)

( * ) Notice: Subject to any disclaimer, the term of this patent is extended or adjusted under 35 U.S.C. 154(b) by 937 days.

(21) Appl. No.: 14/809,058

(22) Filed: Jul. 24, 2015

(65) Prior Publication Data

US 2016/0038028 A1 Feb. 11, 2016

Related U.S. Application Data

(60) Provisional application No. 62/034,699, filed on Aug. 7, 2014.

(51) Int. Cl.

| | | |
|---|---|---|
| *A61B 5/00* | (2006.01) | |
| *A61B 1/04* | (2006.01) | |
| *A61B 5/20* | (2006.01) | |
| *A61B 1/00* | (2006.01) | |
| *A61N 7/02* | (2006.01) | |
| *A61B 18/12* | (2006.01) | |

(Continued)

(52) U.S. Cl.
CPC ........ *A61B 5/0071* (2013.01); *A61B 1/00087* (2013.01); *A61B 1/043* (2013.01); *A61B 1/0638* (2013.01); *A61B 1/307* (2013.01); *A61B 5/0082* (2013.01); *A61B 18/12* (2013.01); *A61N 7/02* (2013.01); *A61B 5/201* (2013.01); *A61B 5/4047* (2013.01); *A61B 5/4052* (2013.01); *A61B 18/1482* (2013.01); *A61B 2018/00404* (2013.01); *A61B 2018/00434* (2013.01); *A61B 2018/00511* (2013.01); *A61B 2090/373* (2016.02); *A61B 2090/376* (2016.02); *A61B 2090/395* (2016.02); *A61B 2090/3937* (2016.02); *A61B 2090/3941* (2016.02); *A61N 2007/003* (2013.01)

(58) Field of Classification Search
CPC combination set(s) only.
See application file for complete search history.

(56) References Cited

U.S. PATENT DOCUMENTS

| | | |
|---|---|---|
| 8,137,274 B2 | 3/2012 | Weng et al. |
| 8,167,805 B2 | 5/2012 | Emery et al. |

(Continued)

OTHER PUBLICATIONS

Hsu; et al., Intraoperative optical imaging and tissue interrogation during urologic surgery. Curr Opin Urol. Jan. 2014;24(1):66-74. doi: 10.1097/MOU.0000000000000010.

(Continued)

*Primary Examiner* — Jason M Ip
(74) *Attorney, Agent, or Firm* — Wilson Sonsini Goodrich & Rosati

(57) ABSTRACT

A target peripheral nerve is treated by providing a real-time fluorescent image of a tissue region where the target peripheral nerve has an enhanced appearance in the fluorescent image. A treatment element is advanced from an adjacent body lumen or cavity through the tissue region or externally aimed toward the peripheral nerve while viewing the fluorescent image, and the peripheral nerve is treated using the treatment element.

13 Claims, 4 Drawing Sheets

(51) Int. Cl.
*A61B 1/307* (2006.01)
*A61B 1/06* (2006.01)
*A61B 18/14* (2006.01)
*A61N 7/00* (2006.01)
*A61B 18/00* (2006.01)
*A61B 90/00* (2016.01)

(56) References Cited

U.S. PATENT DOCUMENTS

| | | |
|---|---|---|
| 8,277,398 B2 | 10/2012 | Weng et al. |
| 8,295,912 B2 | 10/2012 | Gertner |
| 8,372,009 B2 | 2/2013 | Emery et al. |
| 8,374,674 B2 | 2/2013 | Gertner |
| 8,388,535 B2 | 3/2013 | Weng et al. |
| 8,469,904 B2 | 6/2013 | Gertner |
| 8,512,262 B2 | 8/2013 | Gertner |
| 8,517,962 B2 | 8/2013 | Gertner et al. |
| 8,556,834 B2 | 10/2013 | Gertner |
| 8,622,937 B2 | 1/2014 | Weng et al. |
| 8,715,209 B2 | 5/2014 | Gertner |
| 2011/0060324 A1 | 3/2011 | Wu et al. |
| 2013/0165764 A1* | 6/2013 | Scheuermann ...... A61B 5/0095 600/407 |
| 2013/0178824 A1 | 7/2013 | Buelna |
| 2014/0074083 A1* | 3/2014 | Horn ...................... A61B 18/18 606/33 |
| 2014/0107639 A1* | 4/2014 | Zhang ................ A61B 18/1492 606/33 |

OTHER PUBLICATIONS

Whitney; et al., Fluorescent peptides highlight peripheral nerves during surgery in mice. Nat Biotechnol. Apr. 2011;29(4):352-6. doi: 10.1038/nbt.1764. Epub Feb. 6, 2011.

* cited by examiner

RENAL DENERVATION USING NERVE FLUORESCING DYE

CROSS-REFERENCE TO RELATED APPLICATIONS

This application claims the benefit of provisional application 62/034,699, filed on Aug. 7, 2014, the full disclosure of which is incorporated herein by reference.

BACKGROUND OF THE INVENTION

1. Field of the Invention

The present invention relates generally to medical devices, systems, apparatus, and methods for modifying nerve function and treating disease. More particularly, the present invention relates to methods and apparatus for imaging and targeting peripheral nerves in tissue regions surrounding body lumens and cavities, including afferent and efferent nerves within the muscles layers, urothelium and submucosa surrounding the renal pelvis.

Thermally-induced renal neuromodulation via intravascular access is known and described, for example, in U.S. Patent Publication No. 2011/0060324. A catheter is inserted into a vessel in the leg and advanced into a renal artery where the catheter delivers RF energy to the vessel wall in order to damage or ablate the renal nerves. Recent studies have demonstrated that this procedure is not always effective. One reason for poor efficacy is that the nerves vary in location from patient to patient. Since the procedure is done under fluoroscopic imaging with systemic contrast, it is difficult or impossible for a practitioner to know where the nerves are located and to position the RF electrode(s) near the nerves.

An improved renal denervation protocol is described in U.S. Patent Publication No. 2013/0178824 which is commonly owned with the present application. A nerve ablation apparatus is introduced into the renal pelvis of a kidney to treat renal nerves embedded in tissue surrounding the renal pelvis. Access to the renal pelvis may be via the urinary tract or via minimally invasive incisions through the abdomen and kidney tissue. Treatment is effected by exchanging energy, typically delivering heat or extracting heat through a wall of the renal pelvis, or by delivering active substances. While an improvement over intravascular renal nerve denervation, denervation via the renal pelvis also suffers from lack of specificity for particular nerve structures.

Therefore, it would be advantageous to provide visualization of the afferent and efferent renal nerves during a renal denervation procedure to allow improved targeting of specific nerves for treatment. At least some of these objectives will be met by the inventions described below.

2. Description of the Background Art

U.S. Patent Publication Nos. 2011/0060324 and 2013/0178824 have been described above. Hsu et al. (2011) Curr Opin Urol 24:66-74 and Whitney et al. (2014) Nature Biotechnology 29: 352-356, describe fluorescently labeled peptides that preferentially bind to nerve tissue.

SUMMARY OF THE INVENTION

The present invention provides apparatus, systems, and methods for imaging and treating peripheral nerves in a patient. In exemplary embodiments, apparatus, systems, and methods are intended for disrupting, inhibiting, denervating and/or modulating the activity of targeted renal nerves which surround a patient's kidney by exchanging energy or delivering active agents or substances to the renal nerves which lie within the wall of the renal pelvis or adjacent to the renal pelvis within the kidney. Most commonly, such renal denervation and/or modulation will be for the purpose of reducing blood pressure in patients suffering from and/or diagnosed with hypertension, but the methods and apparatus of the present invention could be used for treating patients diagnosed with other conditions as described in U.S. Patent Publication No. 2013/0178824, the full disclosure of which is incorporated herein by reference. The energy exchange or agent delivery is effected through a wall of the renal pelvis, typically using an effector which has been positioned within the interior of the renal pelvis. In other embodiments, the targeted nerves can be treated using external energy sources, such as high intensity focused ultrasound (HIFU), as described in U.S. Pat. Nos. 8,715,209; 8,715,209; 8,622,937; 8,622,937; 8,622,937; 8,622,937; 8,556,834; 8,517,962; 8,517,962; 8,512,262; 8,469,904; 8,388,535; 8,374,674; 8,372,009; 8,295,912; 8,277,398; 8,167,805; and 8,137,274. The full disclosures of which are incorporated by reference.

The renal blood vessels, including the renal arteries and to a lesser extent the renal veins, enter the kidney in a branching network from the main renal artery and main renal vein leading to the kidney. The renal nerves are present in the adventitial tissue surrounding these branching blood vessels as well as in the tissue bed adjacent to the external wall of the renal pelvis. The renal nerves are also in the wall of the renal pelvis in the form of a dense nerve matrix consisting of both afferent and efferent nerves between the muscle layers as well as within the endothelium and submucosa. The present invention provides for enhanced imaging of renal peripheral nerves in tissue surrounding the kidneys and other tissue regions.

In a first aspect of the present invention, a method for targeted treatment of a peripheral nerve in a patient comprises providing a real-time fluorescent image of a tissue region where a target peripheral nerve has an enhanced appearance in the fluorescent image. A treatment element is advanced from an adjacent body lumen or cavity through the tissue region toward the peripheral nerve(s) while viewing the fluorescent image, and the peripheral nerve(s) is/are treated using the treatment element.

In exemplary embodiments, the fluorescent image is produced by injecting a fluorescent label which preferentially binds to nerve tissue within the tissue region and illuminating the tissue region with radiation at a wavelength which excites the fluorescent label. The fluorescent label may be injected systemically or, alternatively or additionally, may be injected locally into the tissue region.

The tissue region is illuminated using a radiation source having a fluorescent or other wavelength selected to excite the fluorescent label to emit a discernable signal, usually a fluorescent or visible light wavelength that can be detected fluoroscopically or optically. In exemplary embodiments, the illumination will be delivered by an endoscope located in the body lumen or cavity, such as a ureteroscope introduced into the renal pelvis of a kidney. In addition to delivering the illumination radiation, the tissue region may be imaged using the ureteroscope or other endoscope to produce the image. The use of optical fibers for delivering and receiving fluorescent and other radiation wavelengths is well known, as is the use of solid state emitters and receivers on endoscopes and similar tools. Any combination of known (or yet to be developed) radiation sources and detectors may be employed for delivery of excitation energy and detection of enhanced images in the methods and systems described below.

While the exemplary methods herein describe imaging using an endoscope, the methods and systems of the present invention may also image the tissue region using an external fluoroscope to produce the image. Similarly, while the exemplary methods herein describe imaging using the endoscope to deliver the treatment, the methods and systems of the present invention may also rely on delivering the treatment from an external source. When using an endoscope, a treatment element may advance from the endoscope. For example, the treatment element may comprise a needle, electrode or other tissue-penetrating element which is advanced into the tissue region. The treatment element will typically deliver energy through the treatment element into the tissue region, wherein the energy usually comprises radiofrequency energy. The treatment element could also be a needle which delivers an ablative solution to the target nerve.

In a second aspect of the present invention, a method for denervating nerves surrounding the renal pelvis comprises injecting a fluorescent label such that the fluorescent label preferentially binds to peripheral nerve tissue in a tissue region surrounding the renal pelvis. Images of the peripheral nerves in tissue region are enhanced by the label, and a treatment element is oriented toward one or more target peripheral nerves within the tissue region while viewing the enhanced images of the peripheral nerves. Target peripheral nerve(s) are treated using the treatment element.

The fluorescent label may be injected systemically or locally into the tissue region. The enhanced fluorescent image may be obtained by illuminating the tissue region with radiation at a wavelength which excites the fluorescent label. Typically, the tissue region is illuminated using a radiation source delivered by an endoscope located in the renal pelvis. The image of the tissue region may be obtained using the endoscope or by using an external fluoroscope to produce the image. Orienting the treatment element typically comprises advancing the treatment element from the endoscope, usually by penetrating the treatment element into the tissue region or placing it in contact or adjacent to the tissue. Treating usually comprises delivering energy through the treatment element into the tissue region, and the energy comprises radiofrequency energy. In alternative embodiments, orienting the treatment element may comprise aiming an external energy source to transcutaneously deliver energy to the target peripheral nerve where, for example, the external energy source may generate high intensity focused ultrasound (HIFU).

In addition to orienting the treatment element, the methods of the present invention may be used to determine the depth and/or size of the target peripheral nerves based on the image and to then calculate at least one of time, power level, temperature, waveform, and frequency need to effectively ablate the target nerves. For example, the imaging unit or a controller may be configured to analyze the size, brightness, and/or other image characteristics to determine the size, pattern and depth of the target nerves. Based on the size, pattern, and depth so determined, the time, intensity and other treatment parameters can be calculated, and energy delivery can be controlled and delivered automatically or delivered manually by the treating physician.

A system for targeted treatment of a peripheral nerve in a patient comprises an endoscopic imaging tool configured to produce a fluoroscopically enhanced image, a nerve treatment element or tool configured to be advanced under endoscopic guidance toward a target peripheral nerve which has been labeled with an injectable fluorescent label, and a controller configured to control the delivery of energy through the treatment element to ablate the target peripherals nerve. Either or both the endoscopic imaging tool and the treatment tool can be configured to be advanced from or through an adjacent body lumen or cavity, and the treatment tool can be further configured to be advanced to the tissue region toward the peripheral nerve while viewing the fluorescent image.

The systems may further comprise the injectable fluorescent label that preferentially binds to peripheral nerve tissue in a tissue region, such as tissue adjacent a renal pelvis. Typically, the controller will include a display for observing the image of the targeted peripheral nerve, and the controller is usually configured to adjust at least one of time, power level, temperature, waveform, and frequency to control the delivery of energy through the treatment element to ablate the target peripherals nerve.

Typically, the fluorescent molecule is excited to emit a certain visible light wavelength. Then the image can be seen directly using the excitation wavelength and white light. But some molecules fluoresce in non-visible wavelengths (e.g. infra-red IR or ultraviolet UV). If using such molecules, an IR or UV sensor/filter must be incorporated into the image acquisition and this must be displayed in visible format on a screen, preferably being overlaid onto the white-light image.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
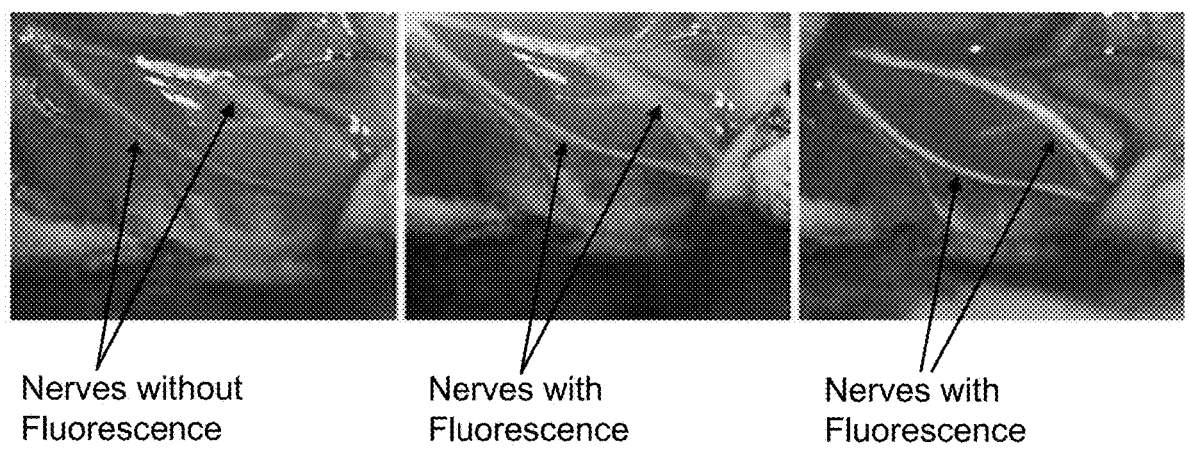
FIG. 1 shows nerves without Fluorescence and with Fluorescence (taken from Hsu et al. (2011) Curr Opin Urol 24:66-74).

In an exemplary preferred embodiment of the invention, a fluorescent label is systemically injected into the patient. The fluorescent label comprises a labelling substance and a peptide or other binding moiety that binds preferentially to nerves. The fluorescent label causes the nerves to fluoresce under certain light or other radiation wavelengths. Specific fluorescent labels and methods for their preparation are described by Hsu et al. (2011) Curr Opin Urol 24:66-74 and Whitney et al. (2014) Nature Biotechnology 29: 352-356, including online methods. Images of the enhanced visualization of peripheral nerves are shown in FIG. 1, taken from Whitney, et al. (2014).

Figure 2:
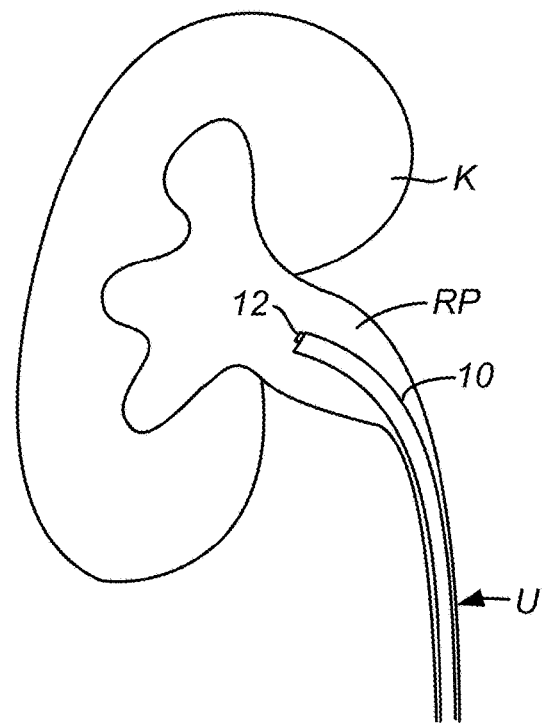
FIG. 2 shows a ureteroscope inserted into the ureter and up to the renal pelvis.
Figure 3:
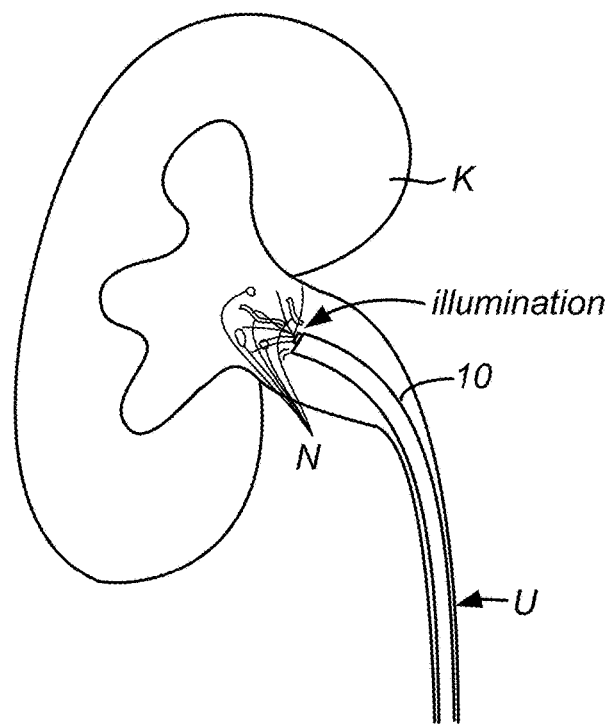
FIG. 3 shows nerves that fluoresce in the renal pelvis wall when illuminated with specific light wavelengths by a fiberoptic ureteroscope.

A ureteroscope 10 is inserted up into the renal pelvis RP via standard urologic techniques as shown in FIG. 2. The ureteroscope has fiber optic illumination 12 and a working channel for advancing a treatment tool as described in more detail below. The illumination can have one or more light wavelengths. By illuminating the tissue bed with one or more wavelengths specific to the injected chemical fluorescers(s), target nerves N in the wall of the renal pelvis RP fluoresce and are easily discernable from surrounding tissue as shown in FIG. 3.

Figure 4:
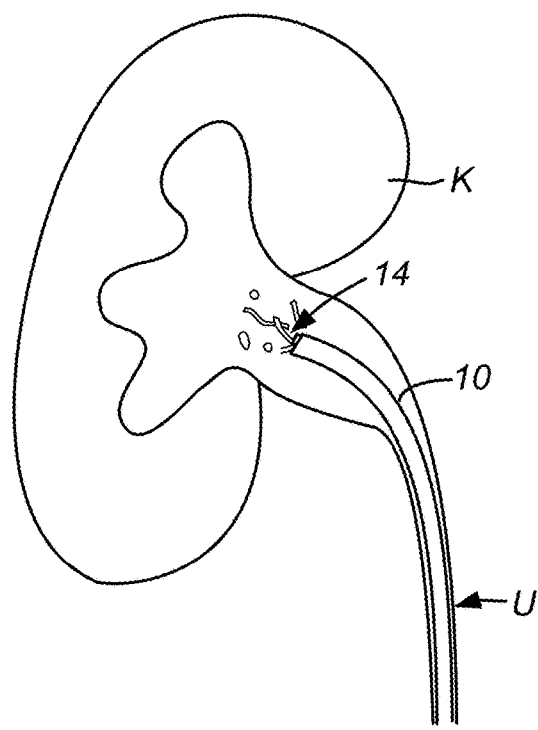
FIG. 4 shows a steerable electrode that is positioned on a target nerve area.

A steerable electrode 14 (or other steerable ablation device such as a microwave antennae, a thermal heating element, a cryogenic element, or a needle to deliver a chemical schlerosing agent, nerve modulating agent, or the like) is then inserted through the working channel of the endoscope 10, and the physician will steer the electrode to the tissue where the target nerves are located by visualization, as shown in FIG. 4. RF energy is then passed through the electrode and into the target tissue, ablating the target nerve(s). Multiple lesions at different locations can be performed in this manner By using fluorescence to locate the nerves and position the electrode, the physician can create the least number of lesions necessary (for safety) while maximizing the effect of the lesions. The renal pelvis approach lends itself to nerve visualization via fluorescent labeling. Vascular approaches cannot use this visualization because of blood. The fluorescent chemical can be injected systemically or it can be injected directly into the renal pelvis or surrounding tissue. Instead of using a fluorescent chemical, dyes can be used to stain tissue to identify nerves.

This general approach can be used at locations along the urinary tract (e.g. ureteropelvic junction, ureter, calices, etc.). Single or multiple electrodes, needles or other treatment elements can be used. Electrode(s) can be expandable nickel-titanium alloy mesh. Electrode(s) can be balloon-based monopolar or bipolar RF electrode(s) can be used. Energy sources other than RF can be used e.g. hot saline, steam, resistance heating, cryoablation, ultrasonic energy, as well as chemical treatments as described above. External treatments, such as HIFU, can also benefit from the enhanced fluoroscopic imaging methods of the present invention.

Instead of approaching the renal pelvis transureterally, the renal pelvis can be approached percutaneously. The fluorescent label or other chemical can be injected with a specialized needle that operates through the working channel of the ureteroscope. The fluorescent label or other chemical can be injected into the target tissue percutaneously.

Instead of using a uretero scope with fiberoptics and a working channel and a steerable sheath, an integrated device can be used. This device would be a steerable catheter with a center lumen for a guide wire, fiberoptic illumination, and one or more integrated electrodes.

In addition to ablating the nerves from inside the renal pelvis or externally using HIFU, the denervation be done laparoscopically. Using standard laparoscopic techniques, the nerves are approached and ablated on the outer wall of the renal pelvis, rather than the inner wall. The laparoscopic approach also allows for ablating target nerves along the outsides of the renal arteries and kidney, specifically the area of the Hilum. Introduction of the label may be sytemic or local, and the illumination may be local via the real pelvis or other adjacent lumen or cavity. In the case of laparoscopic treatments, the illumination can also be accomplished laparoscopically as the treatments tools are being introduced.

In an alternative embodiment, the nerve tissue is excited by one or more wavelengths of light and fluoresces in another wavelength that is not in the visible spectrum (for example Near Infrared). The ureteroscope or other optical sensor that is sensitive to the fluoresced wavelength(s) records the fluorescence. This recorded data is then displayed on a monitor in real time where the invisible wavelengths are converted and displayed as visible wavelengths. This converted image/video can be superimposed in real time onto images/video of the same area as seen in the visible spectrum by the same or another ureteroscope. Tissue is then ablated using methods described previously.

In another alternative embodiment, a ureteroscope with a fiberoptic light source is used to emit a first light wavelength that causes the nerves to fluoresce. The ureteroscope also emits a second light wavelength or wavelengths (typically white) to allow the user to visualize the area in general. In certain cases, the light emitted to visualize the area in general may drown out the fluorescence and make the nerves difficult to distinguish from surrounding tissue. To overcome this, the light sources in the ureteroscope can be selectively turned on and off. For example, the user can use white light to view the area. Then the white light can be switched off and the fluorescent light can be switched on to view the nerves.

The descriptions above refer to targeting individual nerves that fluoresce. However, it is possible that the individual nerves are smaller than what can be reasonably seen with standard surgical ureteroscopes or other scopes. The user may be looking to target areas that are rich in nerve density, rather than just individual nerves. In this case, the areas that are more densely populated with nerves nerve would appear darker in the fluorescing color than surrounding tissue.

An improved renal denervation protocol is described in U.S. Patent Publication No. 2013/0178824 which is commonly owned with the present application. A nerve ablation apparatus is introduced into the renal pelvis of a kidney to treat renal nerves embedded in tissue surrounding the renal pelvis. Access to the renal pelvis may be via the urinary tract or via minimally invasive incisions through the abdomen and kidney tissue. Treatment is effected by exchanging energy, typically delivering heat or extracting heat through a wall of the renal pelvis, or by delivering active substances. In a related invention, the ablation method can include using steam delivered through a catheter or other device to the target tissue. When the steam contacts the tissue, it condenses to liquid, transferring its energy to the tissue. The target tissue can include the renal pelvis, the ureter, the kidney, and the renal arteries and branches.

Figure 5:
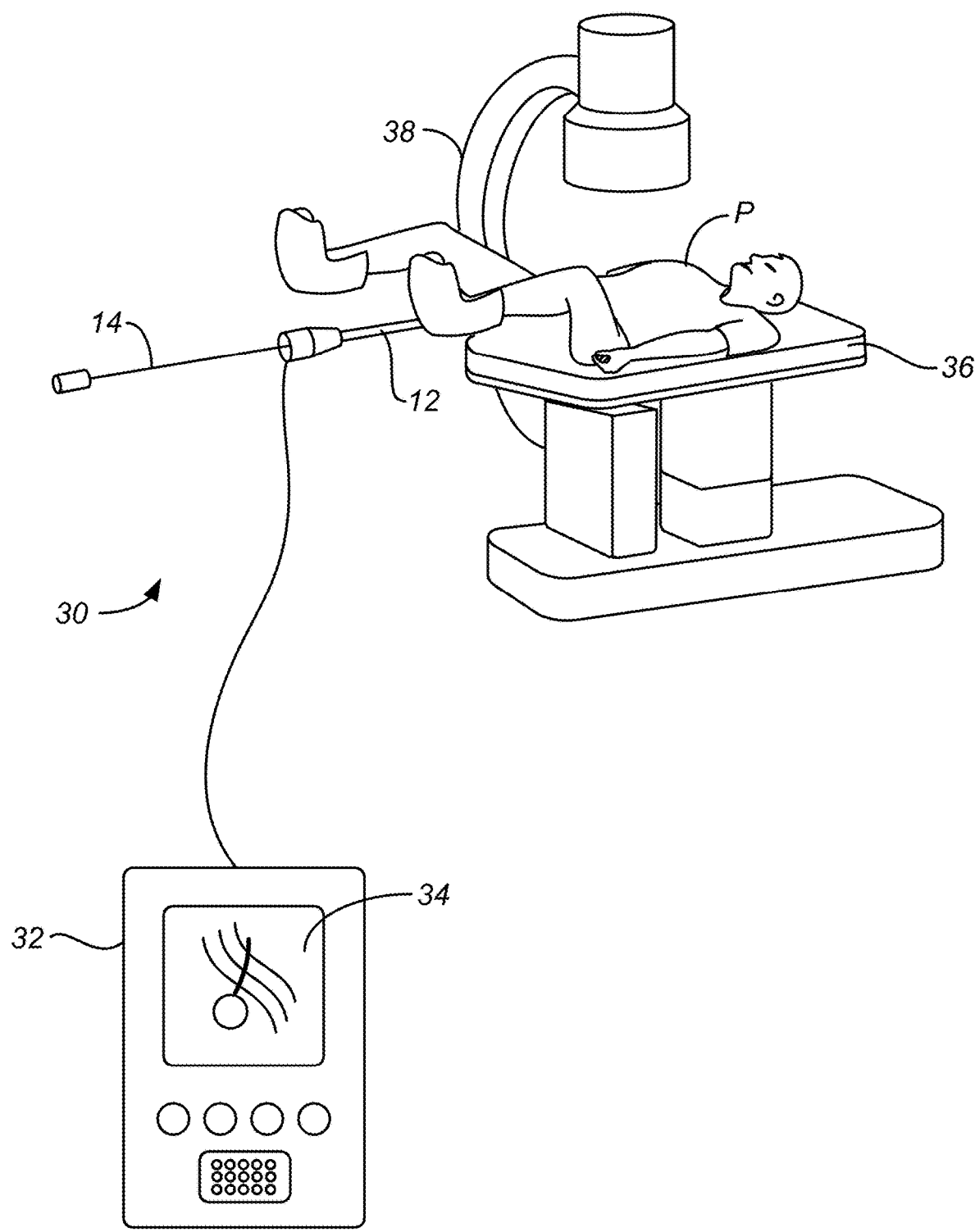
FIG. 5 illustrates a system of the present invention including an endoscope, a treatment tool or effector, and a system controller with an image display.

FIG. 5 illustrates a system 30 of the present invention includes the endoscope 12, a treatment tool or effector 14 configured to be introduced through the ureteroscope into the renal pelvis, and a system controller 32 with an image display 34. A patient P lies on a surgical table 36, and usually a conventional C-arm fluoroscope will be present in case further imaging is needed.

Figure 6:
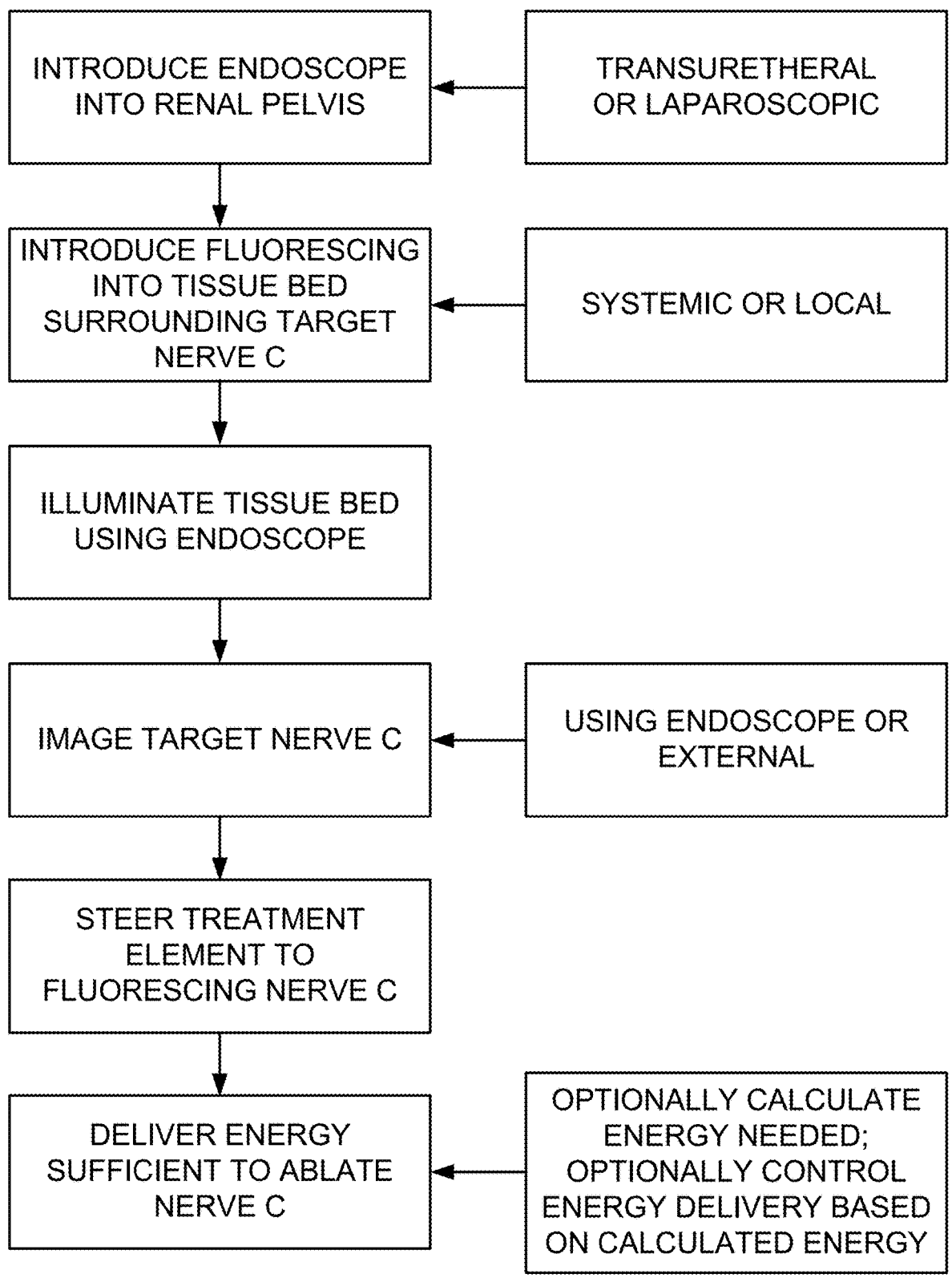
FIG. 6 is a flowchart schematically illustrating the methods of the present invention.

As outlined in FIG. 6, the ureteroscope or other endoscope is transurethrally advanced into the patient's renal pelvis, and a fluorescent dye is locally or systemically introduced into the tissue bed of the renal pelvis to fluorescently tag the nerves. The tissue bed is illuminated with fluorescent excitation energy using a fiberoptic or other illumination source on the endoscope, and the treatment tool, effector, or other element can be steered to a region of high nerve density under direct observation on the display 34 or other available display screen. Once the treatment tool is properly place, the physician can deliver energy through the treatment tool to ablate the nerves. Optionally, the controller can be configured to analyze the image to determine the size, location, and density of the nerve in the renal pelvis wall. That information can further optionally be used to determine the amount of energy that must be delivered in order to ablate the target nerves. Still further optionally, the controller can be configured to automatically control the delivery of energy through the tool in order to deliver the proper amount for the desired ablation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for denervating target peripheral nerves surrounding the renal pelvis, said method comprising:
   injecting a fluorescent label wherein the fluorescent label binds to peripheral nerve tissue in a tissue region surrounding the renal pelvis;
   imaging the tissue region wherein images of the target peripheral nerves are enhanced by the fluorescent label;
   analyzing the size and/or brightness of the enhanced images to determine the depth of the target peripheral nerves;
   calculating treatment time or intensity based on the determined depth of the target peripheral nerves;
   orienting a treatment element toward one or more target peripheral nerves within the tissue region while viewing the enhanced images of the target peripheral nerves;
   treating the target peripheral nerves using the oriented treatment element; and
   controlling energy delivery based on the calculated treatment time or intensity.

2. A method as in claim 1, wherein the fluorescent label is injected systemically.

3. A method as in claim 1, wherein the fluorescent label is injected locally into the tissue region.

4. A method as in claim 1, wherein providing a fluorescent image comprises illuminating the tissue region with radiation at a wavelength which excites the fluorescent label.

5. A method as in claim 4, wherein the tissue region is illuminated using a radiation source delivered by an endoscope located in the renal pelvis.

6. A method as in claim 5, further comprising imaging the tissue region using the endoscope to produce the image.

7. A method as in claim 5, further comprising imaging the tissue region using an external fluoroscope to produce the image.

8. A method as in claim 1, wherein orienting the treatment element comprises advancing the treatment element from an endoscope.

9. A method as in claim 8, wherein advancing the treatment element comprises penetrating the treatment element into the tissue region.

10. A method as in claim 9, wherein treating comprises delivering energy through the treatment element into the tissue region.

11. A method as in claim 10, wherein the energy comprises radiofrequency energy.

12. A method as in claim 1, wherein orienting the treatment element comprises aiming an external energy source to transcutaneously deliver energy to the target peripheral nerve.

13. A method as in claim 12, wherein the external energy source generates high intensity focused ultrasound.

\* \* \* \* \*